ns Patent [19]

United States Patent [19]

Müller et al.

[11] Patent Number: 4,923,996
[45] Date of Patent: May 8, 1990

[54] OPTICALLY ACTIVE RHODIUM COMPLEXES OF 3,4-BIS(DIARYLPHOSPHINO)PYRROLIDINES AND THEIR USE FOR THE PREPARATION OF PHOSPHINOTHRICIN BY ASYMMETRIC HYDROGENATION

[75] Inventors: Wolf-Dieter Müller, Hofheim am Taunus; Hans-Jerg Kleiner, Kronberg, both of Fed. Rep. of Germany

[73] Assignee: Hoechst Aktiengesellschaft, Frankfurt am Main, Fed. Rep. of Germany

[21] Appl. No.: 312,030

[22] Filed: Feb. 17, 1989

[30] Foreign Application Priority Data

Feb. 19, 1988 [DE] Fed. Rep. of Germany ....... 3805151
May 31, 1988 [DE] Fed. Rep. of Germany ....... 3818435

[51] Int. Cl.$^5$ .............................. C07F 9/65; C07F 9/30
[52] U.S. Cl. .................................... 548/402; 548/412
[58] Field of Search ............................... 548/402, 412

[56] References Cited

U.S. PATENT DOCUMENTS 4,168,963 9/1979 Rupp et al. .................... 71/86
4,634,775 1/1987 Beck et al. .................... 548/402

FOREIGN PATENT DOCUMENTS 0151282 12/1984 European Pat. Off. .
2856260 7/1979 Fed. Rep. of Germany .
2717440 4/1984 Fed. Rep. of Germany .
3609818 9/1987 Fed. Rep. of Germany .
872058 3/1987 South Africa .
2011416 7/1979 United Kingdom .

OTHER PUBLICATIONS

Nagel et al., "Synthese N-Substituierter (R,R)-3,4-Bis(Diphenylphosphino)-Pyrrolidine und Anwendung Ihrer Rhodiumkomplexe zur Asymmetrischen Hydrierung von α-(Acylamino Acrylsäure-Derivaten", Chem. Ber., 119 (1986), pp. 3326 to 3343.

"Conformational Analysis in Multisulfur Heterocycles. VI. 3,3:6,6-Bis(Pentamethylene-S-Tetrathiane. Slow Pseudorotation in the Twist Conformer of a 6 Ring", Journal of the American Chemical Society, 93:12, Jun. 16, 1971, pp. 3058-3060.

Primary Examiner—Anton H. Sutto
Assistant Examiner—Edward Rosfjord
Attorney, Agent, or Firm—Curtis, Morris & Safford

[57] ABSTRACT

The invention relates to rhodium complexes of the formula

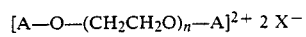

and

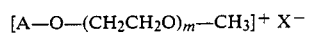

in which
n=5–1,000,
m=5–250,
$X^-$ denotes a tetrafluoroborate, hexafluorophosphate or per-chlorate anion,
A denotes a radical of the formula

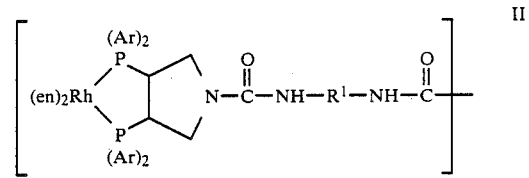

(en)$_2$ denotes two molecules of a monoolefin or one molecule of a diolefin
Ar denotes phenyl or phenyl which is substituted by one or two alkyl groups having 1 or 2 carbon atoms and
R$^1$ denotes an arylene or alkylene bridge, and their use for the preparation of L-phosphinothricin and its derivatives by enantioselective catalytic hydrogenation of 2,3-dehydrophosphinothricin (derivatives).

7 Claims, No Drawings

OPTICALLY ACTIVE RHODIUM COMPLEXES OF 3,4-BIS(DIARYLPHOSPHINO)PYRROLIDINES AND THEIR USE FOR THE PREPARATION OF PHOSPHINOTHRICIN BY ASYMMETRIC HYDROGENATION

The invention relates to novel optically active rhodium complexes of the general formula $$[A-O-(CH_2CH_2O)_n-A]^{2+} 2X^- \qquad Ia$$

and $$[A-O-(CH_2CH_2O)_m-CH_3]^+ X^- \qquad Ib$$

in which
n = 5–1,000,
m = 5–250,
$X^-$ denotes a tetrafluoroborate, hexafluorophosphate or perchlorate anion,
A denotes a radical of the formula

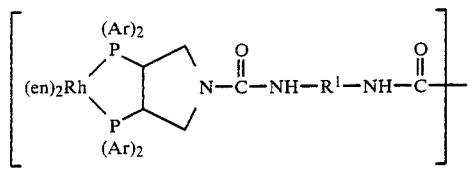

$(en)_2$ denotes two molecules of a monoolefin or one molecule of a diolefin
Ar denotes phenyl or phenyl which is substituted by one or two alkyl groups having 1 or 2 carbon atoms and $R^1$ denotes an arylene or alkylene bridge.

The invention furthermore relates to the use of the catalysts for the preparation of L-homoalanin-4-yl-(methyl)-phosphinic acid (L-phosphinothricin, L-Ptc) and their derivatives by enantioselective catalytic hydrogenation of 2,3-dehydro-phosphinothricin (derivatives).

Phosphinothricin (Ptc) of the formula

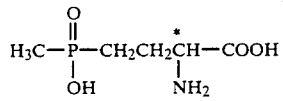

and its esters and salts are known as active herbicides from DE-PS No. 2,717,440 (U.S. Pat. No. 4,168,963). As a result of the asymmetric carbon atom (identified by an asterisk), it occurs in two enantiomeric forms, the L-form of which is the carrier of the physiological activity (DE-OS No. 2,856,260 and GB-A-2,011,416). It is already known that L-Ptc and its derivatives can be prepared by enantioselective (asymmetric) hydrogenation of 2,3-dehydro-phosphinothricin derivatives of the formula

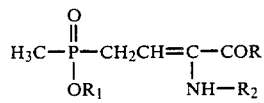

in which
R denotes hydroxyl, $(C_1-C_6)$aloxy, Ala-Ala(OH) or Ala-Leu(OH)
$R_1$ denotes H or $(C_1-C_6)$alkyl and $R_2$ denotes an acyl, alkoxycarbonyl or aryloxycarbonyl radical, by means of rhodium catalysts and subsequent splitting off of the acyl or carboxylic ester radical (DE-OS No. 3,609,818, ZA No. 87/2,058). However, the profitability of the process when carried out on an industrial scale depends on a number of conditions which are met only inadequately by the catalysts described in DE-OS No. 3,609,818.

It is known from Chem. Ber. 119, 3326 (1986) that the solubility of the Rh catalyst in the chosen solvent is a precondition of the hydrogenation, and that the conversion rate (mol of substrate per mol of catalyst per unit time) depends on a catalyst-specific minimum concentration of catalyst. If the concentration falls below this minimum concentration, the conversion rate drops rapidly.

Because of the high costs of Rh catalysts, the profitability of the hydrogenation process also depends on the ratio of the amounts of substrate : catalyst. It goes without saying that the process can be carried out more cheaply the less catalyst is required, that is to say the higher the concentration of the substrate to be hydrogenated, based on the minimum concentration needed for the catalyst. This ratio is influenced decisively by the solvent used.

Since 2,3-dehydro-phosphinothricin and its derivatives are particularly readily soluble in water, it is obvious to choose water as the medium for an economic hydrogenation process. However, the Rh catalysts known from DE-OS No. 3,609,818 are not sufficiently soluble in water, so that the minimum concentration required is not reached. On the other hand, in organic solvents such as methanol, the substrate (2,3-dehydro-phosphinothricin) does not have the optimum solubility, so that the ratio of the amounts of substrate/catalyst is unfavorable.

There was thus the object of discovering rhodium catalysts of good water-solubility which enable 2,3-dehydrophosphinothricin, which is likewise readily soluble in water, to be hydrogenated using a high ratio, that is to say a ratio which is suitable for an economic process, of the amounts of substrate:catalyst. This object is achieved by the catalysts of the formula I according to the invention.

They are obtained by reacting a polyglycol of the formula $HO-(CH_2CH_2O)_n-H$ or a polyglycol monomethyl ether of the formula $HO-(CH_2CH_2O)_m-CH_3$ with a diisocyanate of the formula $R_1(N=C=O)_2$, derivatizing the resulting addition product with a 3,4-bis(diarylphosphino)pyrrolidine of the formula

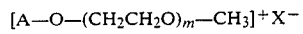

and reacting the reaction product with a rhodium complex of the formula $$[Rh(en)_2Y]_2 \qquad VI$$

(Y = Cl, Br or I) and an alkali metal salt or silver salt of tetrafluoroboric acid, hexafluorophosphoric acid or perchloric acid.

The individual components can be employed in stoichiometric amounts in the process described above for the preparation of the catalysts of the general formulae Ia and Ib according to the invention. Advantageously, however, in the reaction sequence shown, the particular component for new addition is employed in an amount less than the stoichiometric amount, preferably of 5–20 mol %. This should mean that all the new components react as quantatively as possible with the polyglycol or polyglycol monomethyl ether which is becoming progressively more functionalized. It is furthermore advantageous here to allow isocyanate groups still present in the reaction mixture to react by addition of an alcohol, such as ethanol or methanol, before addition of the rhodium component. The catalysts of the formulae Ia and Ib according to the invention are of course not obtained as pure substances in this manner, but as a mixture with compounds which are derived from the general formulae Ia and Ib such that, in the case of compounds of the formulae Ia and Ib, a radical of the general formula II, and in the case of the compounds of the formula Ia, also two radicals of the general formula II, are not built up completely.

In order to allow direct comparison of the hydrogenation activity of the catalysts thus obtained with low molecular weight uniform catalysts which are known from the literature, they are advantageously characterized by an average molecular weight based on rhodium, it being possible for this weight to be easily calculated from the amount of rhodium complex of the formula VI added during the synthesis.

In the starting substances and end products, the individual radicals and substituents have the following meaning.

"en" is a straight-chain, branched or cyclic mono- or diolefin, for example ethylene, 2-butene, butadiene, isoprene, cyclohexene, cyclooctene, 1,5-cyclooctadiene or norbornadiene.

The nature of the radical $R^1$ results from the structure of the diisocyanate employed, for which commercially available di-isocyanates are suitable. Examples of these are hexamethylene diisocyanate, isophorone diisocyanate, diphenylmethane diisocyanate or 2,4-toluylene diisocyanate. Diisocyanates with a graduated reactivity of the individual isocyanate groups, such as, for example, 2,4-toluylene diisocyanate, are particularly suitable.

Suitable polyethylene glycols are those having 5–1,000 EO units (ethyleneoxy units), corresponding to an average molecular weight of about 250 to 45,000. n of 50–250, corresponding to a molecular weight of about 2,000 to about 11,000, are preferred. Suitable polyethylene glycol monomethyl ethers contain 5–250 EO units, corresponding to molecular weights of about 250 to 11,000; m of 50 to 150 $\triangleq$ molecular weight ~2,000 to 6,000 are preferred.

The optically active 3,4-bis(diarylphosphino)pyrrolidines of the general formula V in which "Ar" has the meaning already given are described in Chem. Ber. 113, 3426 (1986) or EP-OS No. 151,282 (U.S. Pat. No. 4,634,775) or can be prepared by the process described therein by reaction of optically active 3,4-dimethanesulfonylpyrrolidinium bromide or acetate with an alkali metal diarylphosphide. If (+)-tartaric acid is used as the starting substance in these multi-stage syntheses, the (R,R)-3,4-bis(diarylphosphino)pyrrolidines are finally obtained.

The rhodium complexes of the formula VI are likewise known from the literature (for example JACS 93, 3059 (1971)), or they can be prepared by processes analogous to those described therein; some of them are even commercially available.

The rhodium complexes of the formula I in which (en)$_2$ denotes a 1,5-cyclooctadiene molecule and X$^-$ denotes a tetrafluoroborate anion can also be prepared in a particularly simple manner by reacting the derivatized 3,4-bis(diarylphosphino)pyrrolidines directly with a rhodium complex of the formula $$[Rh(COD)_2]^+BF_4^- \qquad \text{VII}$$

in which COD stands for 1,5-cyclooctadiene.

The catalysts of the formula I according to the invention are distinguished by a high hydrogenation activity and enantioselectivity during hydrogenation both in water and in organic solvents.

For the abovementioned reasons, they are particularly suitable for asymmetric hydrogenation of IV in an aqueous or water-containing medium. When the (R,R)-3,4-bis(diarylphosphino)pyrrolidine-Rh complex is used, the L-acyl- or L-alkoxy (L-aryloxy)-Ptc is formed in high optical yields.

The hydrogenation is advantageously carried out in water or a mixture of water/alcohol (for example methanol or ethanol). The substrate concentration can extend from a 0.01 molar solution to a solution saturated in substrate. The hydrogen pressure can be between normal pressure and about 80 bar, preferable between 20 and 50 bar, and the reaction temperature can be between 0° and +70° C., preferably between 30° and 50° C. The compounds of the formula I and IV are advantageously employed in amounts such that the molar ratio of substrate to catalyst is as high as possible, and it can be up to 30,000:1. The optimum lies at a ratio of about 10–15,000:1. In contrast, if methanol is used as the solvent, molar ratios of not more than 3,000:1 can be achieved The catalysts according to the invention can also be successfully used in an alcoholic phase, but there are in general no advantages here over the catalysts known from DE-OS No. 3,609,818. The same applies to their use for the asymmetric hydrogenation of other unsaturated acylated amino acids of the α-aminoacrylic acid type

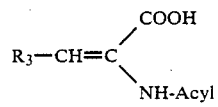

Because of the sensitivity of the optically active 3,4-(diarylphosphino)pyrrolidines and the rhodium complexes according to the invention containing them as chiral ligands towards oxygen, it is advantageous for all the reactions to be carried out under an inert gas atmosphere, for example under nitrogen or argon, and also for the reaction products to be kept under an inert gas. It is moreover advisable also to carry out the hydrogenations under anaerobic conditions.

The following examples are intended to illustrate the invention in more detail, without a limitation thereby being intended.

EXAMPLE 1

Preparation of (3R, 4R)-3,4-bis(di-p-tolylphosphino)pyrrolidine 33.15 g (0.155 mol) of di-p-tolylphosphane and 3.56 g (0.155 mol) of sodium are heated under reflux in 150 ml of tetrahydrofuran until all the sodium has dissolved (about 6 hours). The tetrahydrofuran is stripped off, the residue is taken up in 160 ml of anhydrous dimethylformamide, the mixture is cooled to −20° C. and 13.6 g (40 mmol) of (3S,4S)-3,4-bis(methanesulfonyl)pyrrolidinium bromide (prepared according to EP-OS No. 151,282) are added all at once. The mixture is stirred at this temperature for a further hour and is then placed in the refrigerator overnight. The solvent is stripped off in vacuo, the deep red residue is partitioned between 140 ml of water and 140 ml of diethyl ether, the aqueous phase is extracted once again with 70 ml of diethyl ether, 160 ml of 1 N HCl solution are added to the combined ether phases and the mixture is stirred for 3 hours. The solid which has precipitated is filtered off with suction, rinsed with 50 ml of water and 100 ml of diethyl ether and partitioned between 150 ml of toluene and 60 ml of 1 N sodium hydroxide solution. The organic phase is dried over $Na_2SO_4$ and concentrated to about 20 ml and the product is precipitated with 150 ml of hexane.

Yield: 10.9 g (55% of theory).
Melting point: 74°–76° C.
$[\alpha]_D^{RT} = +106°$ (c=0.7; toluene)
$^{31}$P-NMR (CDCl$_3$)$\delta$(ppm): −8.2, s

EXAMPLE 2

Preparation of the polyethylene glycol (molecular weight 10,000) derivative of [((3R,4R)-3,4-bis-(diphenylphosphpino)pyrrolidine)(COD)Rh]BF$_4$ 10 g (1 mmol) of polyethylene glycol (molecular weight 10,000) are dissolved in 260 g of dioxane in a dried 500 ml flask. 60 g of dioxane are distilled off in order to remove traces of water from the polyethylene glycol. After cooing to room temperature, 0.37 g (2.1 mmol) of 2,4-toluylene diisocyanate are added and the mixture is then stirred overnight. 42 g of the solution are removed for titration for isocyanate. A content of 1.36 mmol of isocyanate results for the remaining solution. 0.53 g (1.2 mmol) of (3R,4R)-3,4-bis-(diphenylphosphino)pyrrolidine (prepared according to EP-OS No. 151,282) is added, the mixture is stirred for 2 hours and then 15 ml of methanol and after a further 15 minutes 0.41 g (1 mmol) of [Rh(COD)$_2$a BF$_4$ are added. After stirring overnight, the mixture is concentrated to about 40 ml in vacuo and the product is precipitated by addition of 200 ml of hexane. 9.1 g (99% of theory) of the pale yellow product of melting point 52°–55° C. are obtained by filtration with suction and drying under a high vacuum.

Average molecular weight, based on rhodium: 9,100

EXAMPLE 3

Preparation of the polyethylene glycol (molecular weight 10,000) derivative of [((3R,4R)-3,4-bis-(di-p-tolylphosphino)pyrrolidine)(COD)Rh]BF$_4$ 10 g (1 mmol) of polyethylene glycol (molecular weight 10,000) and 0.37 g (2.1 mmol) of 2,4-toluylene diisocyanate are reacted analogously to Example 2. After stirring overnight, 20% of the batch is removed for titration for isocyanate. A content of 1.52 mmol of isocyanate results for the remaining solution. 0.65 (1.3 mmol) of the (3R,4R)-3,4-bis(di-p-tolylphosphino)pyrrolidine prepared according to Example 1 are added, the mixture is stirred for 2 hours and then 15 ml of methanol and after a further 15 minutes 0.45 g (1.1 mmol) of [Rh(COD)$_2$]BF$_4$ are added. After stirring overnight, the mixture is concentrated to about 40 ml in vacuo and the product is precipitated by addition of 200 ml of hexane. 9.3 g (100% of theory) of the pale yellow product of melting point 53°–55° C. are obtained after filtration with suction and drying under a high vacuum.

Average molecular weight, based on rhodium: 8,400.

EXAMPLE 4

Preparation of the polyethylene glycol monomethyl ether (molecular weight 5,000) derivative of [((3R,4R)-3,4-bis-(tolylphosphino)pyrrolidine)(COD)Rh]BF$_4$ 10 g (2 mmol) of polyethylene glycol monomethyl ether (molecular weight 5,000) and 0.37 g (2.1 mmol) of 2,4-toluylene diisocyanate are reacted analogously to Example 2. After stirring overnight, 20% of the batch are removed for titration for isocyanate. A content of 1.4 mmol of isocyanate results for the remaining solution. 0.59 g (1.2 mmol) of (3R,4R)-3,4-bis(di-p-tolylphosphino)pyrrolidine prepared according to Example 1 is added, the mixture is stirred for 2 hours and then 15 ml of methanol and after a further 15 minutes 0.41 g (1 mmol) of [Rh(COD)$_2$]BF$_4$ are added. After stirring overnight, the mixture is concentrated to about 40 ml in vacuo and the product is precipitated by addition of 200 ml of hexane. 8.9 g (97% of theory) of the pale yellow product of melting point 55.5°–58° C. are obtained after filtration with suction and drying under a high vacuum.

Average molecular weight, based on rhodium: 9,200.

EXAMPLE 5

Preparation of the polyethylene glycol (molecular weight 350) monomethyl ether derivative of [((3R,4R)-3,4-bis-(diphenylphosphino)pyrrolidine)(COD)Rh]BF$_4$ 1.05 g (3 mmol) of polyethylene glycol (molecular weight 350) monomethyl ether are dried at 40° C. under a high vacuum for 2 hours and then taken up in 40 ml of absolute dioxane, and 10 ml of dioxane are distilled off in order to remove the last traces of water. 0.52 g (3 mmol) of 2,4-toluylene diisocyanate are added and the mixture is stirred overnight. 20% of the batch is removed for titration for isocyanate. A content of 2 mmol of isocyanate results for the remaining solution. 0.79 g (1.8 mmol) of (3R,4R)-3,4-bis(diphenylphosphino)pyrrolidine (prepared according to EP-OS No. 151,282) is added, the mixture is stirred for 2 hours and then 5 ml of methanol and after a further 15 minutes 0.67 g (1.65 mmol) of [Rh(COD)$_2$]BF$_4$ are added. After stirring overnight, the solvent is stripped off and the residue is dried under a high vacuum.

Yield: 2.49 g (98% of theory) of pale yellow melting point 81°–85° C.

Average molecular weight, based on rhodium: 1.550.

EXAMPLE 6

Hydrogenations with the rhodium complex prepared according to Example 2

66 mg of the rhodium complex are dissolved under inert gas in a degassed solution of 17.6 g of N-acetyl-2,3-dehydrophosphinothricin (Δ-Ac-Ptc, prepared according to DE-OS No. 3,609,818) in 50 ml of water. This solution is introduced, in counter-current with $N_2$, into a 200 ml stainless steel autoclave which has a glass insert and magnetic stirrer and has first been freed from oxygen by means of $N_2$.

After flushing with $H_2$, $H_2$ is forced in up to a pressure of 50 bar, the autoclave is heated to 50° C. and the stirrer is started. After 18 hours, the $H_2$ uptake has ended and the pressure has fallen to 34 bar. The autoclave is let down and emptied. A 6 N hydrochloric acid solution is prepared by addition of an equivalent amount of concentrated hydrochloric acid to the reaction solution and is heated under reflux for 8 hours. The solution is concentrated and the residue is boiled up with 40 ml of ethanol, in order to dissolve the catalyst constituents, and then filtered off with suction, rinsed with 15 ml of ethanol and dried.

Conversion: 100%.

Yield of L-phosphinothricin hydrochloride: 16.5 g (95.3% of theory). Melting point: 194°–197° C. (decomposition).

$[\alpha]_D^{22} = +23.2°$ (c=1; 1 N HCl).

This corresponds to an optical yield of 89.9% based on $[\alpha]_D^{22} = +25.8°$ (c=1; 1 N HCl) for optically pure L-phosphinothricin hydrochloride (DE-OS No. 3,609,818).

(b) Comparison

Analogously to Example 6a, 73 mg of the rhodium complex are dissolved in 50 ml of a methanolic solution saturated with 4.4 g of Δ-Ac-Ptc and the mixture is hydrogenated at 30° C. under an initial $H_2$ pressure of 30 bar. After 2 hours, the $H_2$ uptake has ended. The autoclave is let down, the reaction solution is concentrated and the residue is taken up in 6 N hydrochloric acid. Further working up is carried out analogously to Example 6a. Conversion 100%.

Yield of L-phosphinothricin hydrochloride: 4.0 g (92.4% of theory); $[\alpha]_D^{22} = +23.3°$ (c=1; 1 N HCl) corresponding to an optical yield of 90.3%.

If the amounts used are 8.8 g of Δ-Ac-Ptc and 73 mg of the rhodium complex in 50 ml of water under an initial $H_2$ pressure of 50 bar at 30° C., the hydrogenation has ended after 8 hours. 8.1 g (93.5% of theory) of L-phosphinothricin hydrochloride with an optical rotation $[\alpha]_D^{22}$ of +23.0° (c=1; 1 N HCl), corresponding to an optical yield of 89.1%, are obtained.

EXAMPLE 7

Hydrogenations with the rhodium complex prepared according to Example 3

8.8 g of Δ-Ac-Ptc and 67 mg of the rhodium complex are hydrogenated in 50 ml of water at 30° C. under an initial $H_2$ pressure of 50 bar analogously to Example 6. After 8 hours, the $H_2$ uptake has ended. 8.0 g (92.4% of theory) of L-phosphinothricin hydrochloride with an optical rotation $[\alpha]_D^{22}$ of +22.4° (c=1; 1 N HCl), corresponding to an optical yield of 86.8%, are obtained.

(b) Comparison

The hydrogenation of a saturated solution of 4.4 g of Δ-Ac-Ptc and 67 mg of the rhodium complex in 50 ml of methanol at 30° C. under an initial $H_2$ pressure of 35 bar gives, after 1.5 hours, 3.9 g (90.1% of theory) of L-phosphinothricin hydrochloride with an optical rotation of $[\alpha]_D^{22} = +23.2°$ (c=1; 1 N HCl), corresponding to an optical yield of 89.9%.

EXAMPLE 8

Hydrogenations with the rhodium complex prepared according to Example 4

8.8 g of Δ-Ac-Ptc and 74 mg of the rhodium complex are hydrogenated in 50 ml of water at 30° C. under an initial $H_2$ pressure of 35 bar analogously to Example 6. After 3 hours, the $H_2$ uptake has ended. 4.0 g (92.4% of theory) of L-phosphinothricin hydrochloride with an optical rotation of $[\alpha]_D^{22} = _D +22.3°$ (C=1; 1 N HCl) corresponding to an optical yield of 86.4%, are obtained.

(b) Comparison

Hydrogenation of a saturated solution of 4.4 g of Δ-Ac-Ptc in 50 ml of methanol with the addition of 74 mg of the rhodium complex at 30° C. under an initial $H_2$ pressure of 35 bar gives, after 1.5 hours, 3.9 g (90.1% of theory) of L-phosphinothricin hydrochloride with an optical rotation of $[\alpha]_D^{RT}$ of +23.7° (c=1; 1 N HCl), corresponding to an optical yield of 91.9%.

What is claimed is:

1. A rhodium complex of the formula $$[A-O-(CH_2CH_2O)_n-A]^{2+} 2X^- \qquad \text{Ia}$$

and $$[A-O-(CH_2CH_2O)_m-CH_3]^+ X^- \qquad \text{Ib}$$

in which
n = 5–1,000,
m = 5–250,
$X^-$ a tetrafluoroborate, hexafluorophosphate or perchlorate anion,
A is a radical of the formula

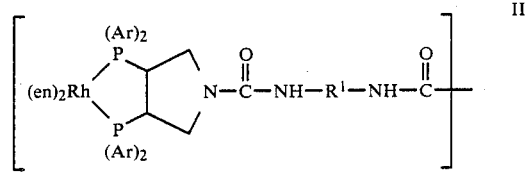

(en)$_2$ represents two molecules of a monoolefin or one molecule of a diolefin
Ar is phenyl or phenyl which is substituted by one or two alkyl groups having 1 or 2 carbon atoms and
$R^1$ is an arylene or alkylene bridge.

2. A rhodium complex of the formula Ia as claimed in claim 1, in which n is 50 to 250, corresponding to an average molecular weight of 2,000 to 11,000.

3. A rhodium complex of the formula Ib as claimed in claim 1, in which m is 50 to 150, corresponding to an average molecular weight of 2,000 to 6,000.

4. A rhodium complex as claimed in claim 1, in which $R^1$ is the divalent alkylene or arylene radical of a diisocyanate from the group comprising hexamethylene diisocyanate, isophorone diisocyanate, diphenylmethane diisocyanate and 2,4-toluylene diisocyanate.

5. A rhodium complex as claimed in claim 4, in which $R^1$ is 2,4-toluylene diisocyanate.

6. A process for the preparation of a rhodium complex of the formula Ia or Ib as defined in claim 1, which comprises reacting a polyglycol of the formula HO—$(CH_2CH_2O)_n$—H or a polyglycol monomethyl ether of the formula HO—$(CH_2CH_2O)_m$—$CH_3$ with a diisocyanate of the formula $R_1(N{=}C{=}O)_2$, derivatizing the resulting addition product with a 3,4-bis(diarylphosphino)pyrrolidine of the formula

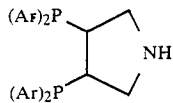

V and reacting the reaction product with a rhodium complex of the formula

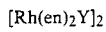

VI (Y=Cl, Br or I) and an alkali metal salt or silver salt of tetrafluoroboric acid, hexafluorophosphoric acid or perchloric acid.

7. A process for the preparation of a rhodium complex of the formula Ia or Ib as defined in claim 1, in which $(en)_2$ is 1,5-cyclooctadiene, and $X^-$ is tetrafluoroborate, which comprises reacting a polyglycol of the formula HO—$(CH_2CH_2O)_n$—H or a polyglycol monomethyl ether of the formula HO—$(CH_2CH_2O)_m$—$CH_3$ with a diisocyanate of the formula $R^1(N{=}C{=}O)_2$, derivatizing the resulting addition product with a 3,4-bis(diarylphosphino)pyrrolidine of the formula

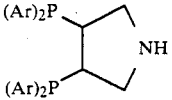

V and reacting the reaction product with a rhodium complex of the formula

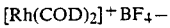

in which COD denotes 1,5-cyclooctadiene.

* * * * *